(12) United States Patent
Regan et al.

(10) Patent No.: US 8,647,573 B2
(45) Date of Patent: Feb. 11, 2014

(54) AUTOMATED DIAGNOSTIC KIOSK FOR DIAGNOSING DISEASES

(75) Inventors: John Frederick Regan, San Mateo, CA (US); James Michael Birch, Albany, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 790 days.

(21) Appl. No.: 12/712,345

(22) Filed: Feb. 25, 2010

(65) Prior Publication Data

US 2010/0152885 A1 Jun. 17, 2010

Related U.S. Application Data

(62) Division of application No. 12/039,069, filed on Feb. 28, 2008.

(60) Provisional application No. 60/904,540, filed on Mar. 2, 2007, provisional application No. 60/904,505, filed on Mar. 2, 2007.

(51) Int. Cl.
*G01N 27/00* (2006.01)

(52) U.S. Cl.
USPC .......................................................... 422/63

(58) Field of Classification Search
USPC .......................................................... 422/63
See application file for complete search history.

(56) References Cited

U.S. PATENT DOCUMENTS

| | | | |
|---|---|---|---|
| 4,713,974 A * | 12/1987 | Stone | 73/864.23 |
| 5,234,809 A | 8/1993 | Boom et al. | |
| 5,544,649 A | 8/1996 | David et al. | |
| 6,335,166 B1 * | 1/2002 | Ammann et al. | 435/6 |
| 6,638,218 B2 * | 10/2003 | Bulat | 600/300 |
| 2002/0064881 A1 * | 5/2002 | Devlin et al. | 436/43 |
| 2006/0111620 A1 * | 5/2006 | Squilla et al. | 600/300 |

FOREIGN PATENT DOCUMENTS

| | | |
|---|---|---|
| WO | WO 99/04043 | 1/1999 |
| WO | WO 02/23459 | 3/2002 |

OTHER PUBLICATIONS

Porter et al. "The Asthma Kiosk: A Patient-centered Technology for Collaborative Decision Support in the Emergency Department" Journal of the American Medical, Informatics Association, vol. 11 No. 6, pp. 458-466, Nov./ Dec. 2004.

Kreuter et al. "Use of computer kiosks for breast cancer education in five community settings" Health Education & Behavior, vol. 33 (5): 625-642, Oct. 2006.

(Continued)

*Primary Examiner* — Jonathan Hurst
(74) *Attorney, Agent, or Firm* — Eddie E. Scott

(57) ABSTRACT

An automated and autonomous diagnostic apparatus that is capable of dispensing collection vials and collections kits to users interesting in collecting a biological sample and submitting their collected sample contained within a collection vial into the apparatus for automated diagnostic services. The user communicates with the apparatus through a touch-screen monitor. A user is able to enter personnel information into the apparatus including medical history, insurance information, co-payment, and answer a series of questions regarding their illness, which is used to determine the assay most likely to yield a positive result. Remotely-located physicians can communicate with users of the apparatus using video tele-medicine and request specific assays to be performed. The apparatus archives submitted samples for additional testing. Users may receive their assay results electronically. Users may allow the uploading of their diagnoses into a central databank for disease surveillance purposes.

1 Claim, 14 Drawing Sheets

(56) References Cited

OTHER PUBLICATIONS

Miller, Judith "U.S. is deploying a monitor system for germ attacks" nytimes.com, Jan. 22, 2003.

Cole, Sally "Biodetectors evolving, monitoring U.S. cities" PennWell Corporation, Homeland Security Solutions, May 2003.

Cassel, Dana "Generic-sampling ATMs: Friend or foe?" Drug topics Supplements, http://www.drugtopics.com, Apr. 3, 2006.

"New diagnostic tool aids in pathogen identification; kiosks in doctors' offices provide generic drug samples" Modern Medicine, http://www.modernmedice.com, Feb. 1, 2007.

* cited by examiner

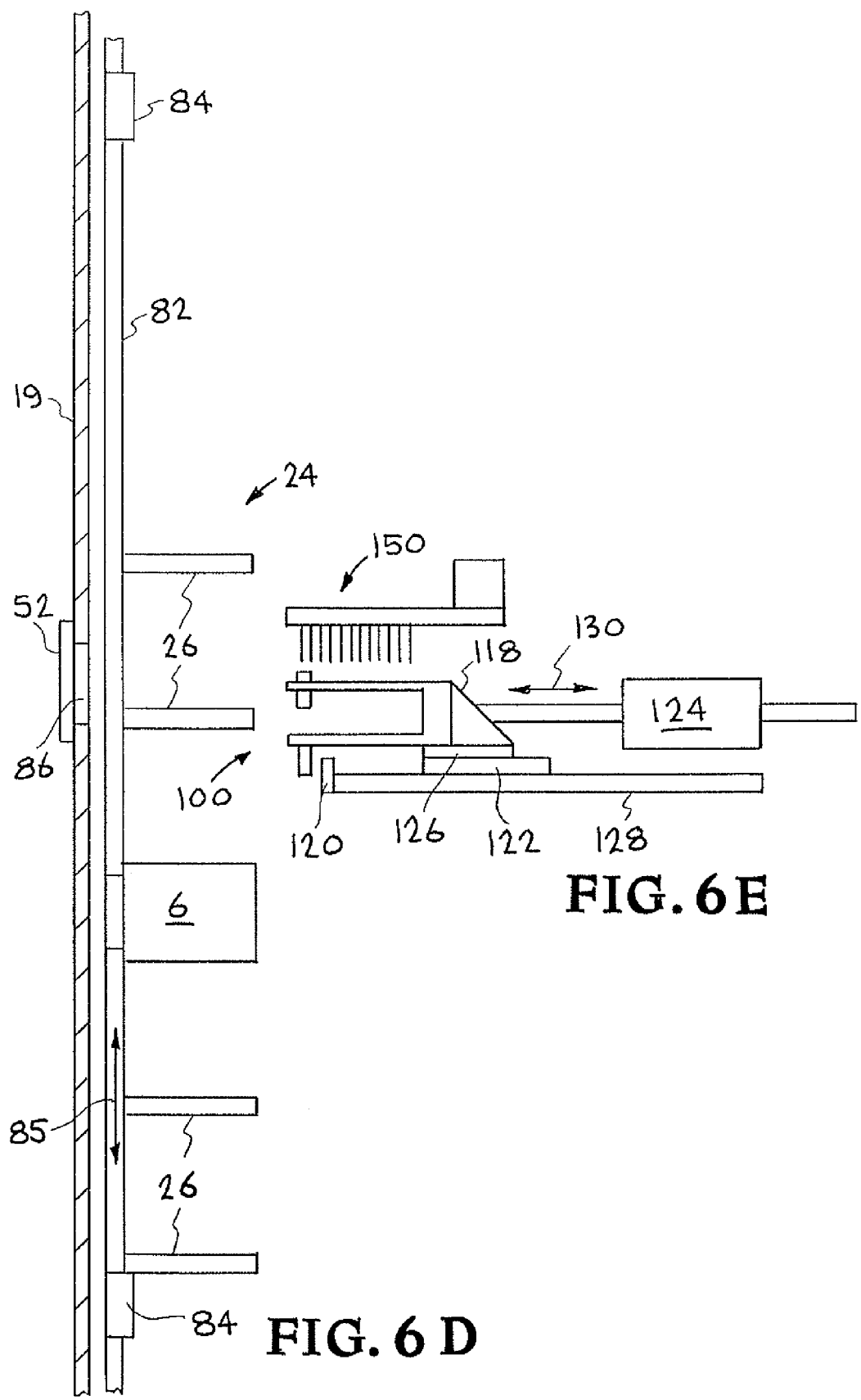

AUTOMATED DIAGNOSTIC KIOSK FOR DIAGNOSING DISEASES

CROSS-REFERENCE TO RELATED APPLICATIONS

This application is a Divisional of application Ser. No. 12/039,069 filed Feb. 28, 2008 and titled "Automated Diagnostic Kiosk for Diagnosing Diseases" which claims the benefit of U.S. Provisional Patent Application No. 60/904,540 filed Mar. 2, 2007 by John Frederick Regan and James Michael Birch titled "Automated Networked Diagnostic Kiosk" and U.S. Provisional Patent Application No. 60/904,505 filed Mar. 2, 2007 by John Frederick Regan titled "Automated High-Throughput Flow-Through Real-Time Fluorescence Detector," which are incorporated herein by this reference.

STATEMENT AS TO RIGHTS TO INVENTIONS MADE UNDER FEDERALLY SPONSORED RESEARCH AND DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to diagnosis and more particularly to a diagnostic kiosk or diagnostic station for diagnosing diseases.

2. State of Technology

The article, "The Asthma Kiosk: A Patient-centered Technology for Collaborative Decision Support in the Emergency Department" by Stephen C. Porter, Zhaohui Cai, William Gribbons, Donald A. Goldmann, and Isaac S. Kohane in *J Am Med Inform Assoc.* 2004 November-December; 11(6): 458-467. doi: 10.1197/jamia.M1569 provides the following state of technology information. "The Asthma Kiosk is a patient-centered technology that promotes capture of critical information necessary to drive guideline-based care for pediatric asthma. The design of this application, the asthma kiosk, addresses five critical issues for patient-centered technology that promotes guideline-based care: (1) a front-end mechanism for patient-driven data capture, (2) neutrality regarding patients' medical expertise and technical backgrounds, (3) granular capture of medication data directly from the patient, (4) formal algorithms linking patient-level semantics and asthma guidelines, and (5) output to both patients and clinical providers regarding best practice. The formative evaluation of the asthma kiosk demonstrates its ability to capture patient-specific data during real-time care in the emergency department (ED) with a mean completion time of 11 minutes. The asthma kiosk successfully links parents' data to guideline recommendations and identifies data critical to health improvements for asthmatic children that otherwise remains undocumented during ED-based care."

The article, "Use of Computer Kiosks for Breast Cancer Education in Five Community Settings" by Matthew W. Kreuter et a provides the following state of technology information: "The use of kiosks to deliver health information is growing rapidly (Science Panel on Interactive Communication and Health, 1999). In published studies alone, kiosk-based programs have been used to assess cancer risk (Strecher, 1999; Westman, Hampel, & Bradley, 2000); assist in asthma management (Porter, Cai, Gribbons, Goldmattn, & Kohane, 2004); identify and manage different types of headaches (Schneider, Furth, Blalock, & Sherrill, 1999); provide general medical information (Nicholas, Huntington, Williams, & Vickery, 2001); teach safe sex negotiation skills (Thomas, Cahill, & Santilli, 1997); educate about Alzheimer's disease (Connell et al., 2003), skin cancer {Lindholm, Isacsson, Slaug, & Moller, 1998), diabetes management (Lewis & Nath, 1997), food safety {Endres, Welch, & Perseli, 2001), and tuberculosis management (Hripcsak et al., 1999); and promote weight loss (Wylie-Rosett et al., 2001) . . . . Studies of naturalistic kiosk use in community settings have been relatively rare. The largest known project, the Michigan Interactive Health Kiosk Project, put 100 computer kiosks addressing 10 different health topics in community centers, super-markets, shopping malls, YMCAs, and local health departments throughout Michigan (Strecher, 1999). Although usage was estimated at 400,004 annually and some information suggested a diverse base of users, no systematic evaluation of kiosk use has yet been reported. The most comprehensive community usage study 'to date was conducted by Radvan, Wiggers, and Hazell (2004), who observed exposure to and use of a multitopic health information kiosk placed in shopping centers, health care facilities, licensed clubs (places where gambling is permitted), and a cinema complex in New South Wales, Australia."

International Patent Publication No. WO2/002023459 for a system for medication dispensing and integrated data management by Medvantix Inc. provides the following state of technology information: "Prescription Dispensing Procedure Current prescription filling methods and processes are inadequate and inefficient. First, an authorized caregiver, usually a doctor, writes a prescription on a pre-printed prescription pad. The patient selects a retail pharmacy, usually based upon insurance coverage, and presents the handwritten prescription for filling. The pharmacy puts the prescription into a preparation queue and when the prescription reaches the top of the queue, the pharmacy enters the prescription into its own records or system. If necessary, the pharmacy personnel place calls (callbacks) to the medical office to clarify or notify MD of issues or questions. Some of the reasons for these callbacks are: clinical issues, quantity issues or recommend medication change (these examples are not conclusive). The pharmacy selects the prescription medication according to prescription benefits manager (PBM) guidelines. The prescription is taken from stock within the pharmacy, prepared, bottled and labeled. The patient receives the medication and required counseling from the pharmacist. The patient then pays a co-pay if required. The pharmacy retains the details of the prescription for refilling. International Patent Publication No. WO2/002023459 claims a medical system for integrating data management with the process of controllably dispensing products including medications, the system comprising: one or more dispensers configured to controllably release a product in response to a control signal; an admission subsystem configured to maintain patient information; and a prescription subsystem coupled to said one or more dispensers and configured to receive entry of prescription information, to relate patient information from said admission subsystem to the prescription information to initiate a determination of whether the product is appropriate for the patient, and to send a control signal to said one or more dispenser units to release the product.

U.S. Pat. No. 6,638,218 for a system and method for delivering medical examination, diagnosis, and treatment over a network issued to Paul I. Bulat and assigned to American Doctors On-Line, Inc. Oct. 28, 2003 provides the following state of technology information: "Health care costs in the United States exceed one trillion dollars per year. In 1996, spending on health care in the United States exceeded fourteen percent of the Gross Domestic Product. Current health care system costs include annual service to over ninety million people in over five thousand hospital emergency departments. These ninety million or more visits impose an enormous burden on emergency departments. Ambulances on route toward the closest available emergency department are often diverted to other hospitals, sometime located in another city. The cause of such calamities is multi-factorial and includes: nursing shortages, bed unavailability, and grossly overcrowded, overburdened emergency rooms. Telecommunications technologies, and in particular, video-conferencing, offer an opportunity to provide cost effective care in a variety of settings. In particular, tele-medicine and tele-healthcare have been envisioned with respect to many specialties including: pathology, dermatology, surgery, ophthalmology, cardiology, and radiology. However, diagnosis and treatment in these areas require either a human presenter or mechanical equipment at the patient end to gather pertinent information related to the patient's condition."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a diagnostic apparatus for analyzing samples from patients. The diagnostic apparatus includes a body unit; a sample acquisition unit in the body unit that acquires samples from patients; a diagnostic instrument in the body unit that analyzes samples and produces diagnoses for patients, and a control in the body unit that is connected to the sample acquisition unit and the diagnostic instrument.

In one embodiment the present invention provides an Autonomous Diagnostic Vending Machine (ADVM) for analyzing samples from patients. The ADVM contains robotic equipment to dispense collection vials to users interested in having a biological sample analyzed for a disease, syndrome, or condition. The patient collects and places a biological sample (e.g. nasal swab) into a collection vial that is submitted into the ADVM for automated diagnostic services.

The ADVM performs molecular analysis on a portion of the submitted sample and archives the remaining sample for possible further confirmatory testing. Depending on the degree of use, ADVMs can operate for more than a month without requiring maintenance. ADVMs provide many of the same services available from advanced clinical diagnostic laboratories. They are ideal for all types of settings, ranging from busy emergency rooms where these instruments can help triage patients, to rural settings where sending samples to remote diagnostic laboratories is both time consuming and costly. ADVMs are also equipped with video-telemedicine capabilities that enable doctors to see and speak with individuals in remote areas that do not have immediate access to specialists. In addition, ADVMs may be placed in public locations (e.g. pharmacies) and equipped with pay station capabilities to enable the general public to provide a co-payment fee for access to an ADVM's diagnostic services, without having to make an appointment to see a physician.

ADVMs deployed to publicly accessible areas such as pharmacies, may prove to be an effective way to reduce overcrowding in emergency rooms and also help reduce the overall cost of delivering healthcare. A user of a publicly deployed ADVM can return to the comfort of their home to wait for their results, which may take less than one hour from the time the sample was deposited in the machine. Results can be electronically delivered to the user via email, text message, pager, or through to a secure website. Prior to or just after receiving results, users may also receive a phone call from a remotely-located physician (240) that monitors ADVM data. The monitoring physician, equipped with a positive diagnosis from an ADVM, is better prepared to prescribe the proper medication or suggest an over-the-counter remedy that may help alleviate the user's symptoms than a physician seeing a patient for the first time in person for whom a diagnosis has not yet been determined. The placement of ADVMs in pharmacies makes picking up medications for diagnosed illnesses especially convenient since prescriptions can be wired directly to the hosting pharmacy. Likewise, individuals infected with untreatable non-life-threatening diseases may be advised to rest at home and not return to work until their infection has passed. For instances where the diagnosis is more dire or inconclusive, remotely-located ADVM monitoring physicians can advise these individuals to either wait for an ambulance to arrive, or immediately transport themselves to the nearest hospital that has been notified in advance of their arrival and is prepared to receive them.

The AVDM is similar in size and shape to a soda vending machine. The AVDM is composed of a computer, touch-screen monitor, collection kits and vials; machinery to dispense collection vials to users, receive the collected sample vials, and delivered them to an automated multi-channel diagnostic instrument for automated processing; a video camera with audio capabilities, a pay station, and a waste receptacle.

The automated instrument within an ADVM can be any automated instrument. By way of example, the described ADVM is equipped with a high throughput flow-through real-time instrument as described and claimed in the U.S. Provisional Patent Application No. 60/904,505 filed Mar. 2, 2007 by John Frederick Regan titled "Automated High-Throughput Flow-Through Real-Time Fluorescence Detector" referenced in the Cross Reference to Related Applications section above and in U.S. patent application Ser. No. 12/038,109 title "Automated High-Throughput Flow-Through Real-Time Diagnostic System" by John Frederick Regan filed Feb. 27, 2008.

This instrument is capable of processing 12 samples in an asynchronous and parallel fashion for an unlimited number of genetic sequences. The instrument is extremely sensitive as it performs nucleic acid extraction and purification before performing the genetic assay. This diagnostic instrument is capable of detecting pathogens (viruses, bacteria, fungi, molds, parasites, etc.) as well as identifying the presence of genetic mutations that may cause other diseases, such as cancer, syndromes, and conditions due to genetic abnormalities.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

FIGS. 6A, 6B, 6C, and 6E illustrate the vial acquisition head of the ADVM.

DETAILED DESCRIPTION OF THE INVENTION

Figure 1A:
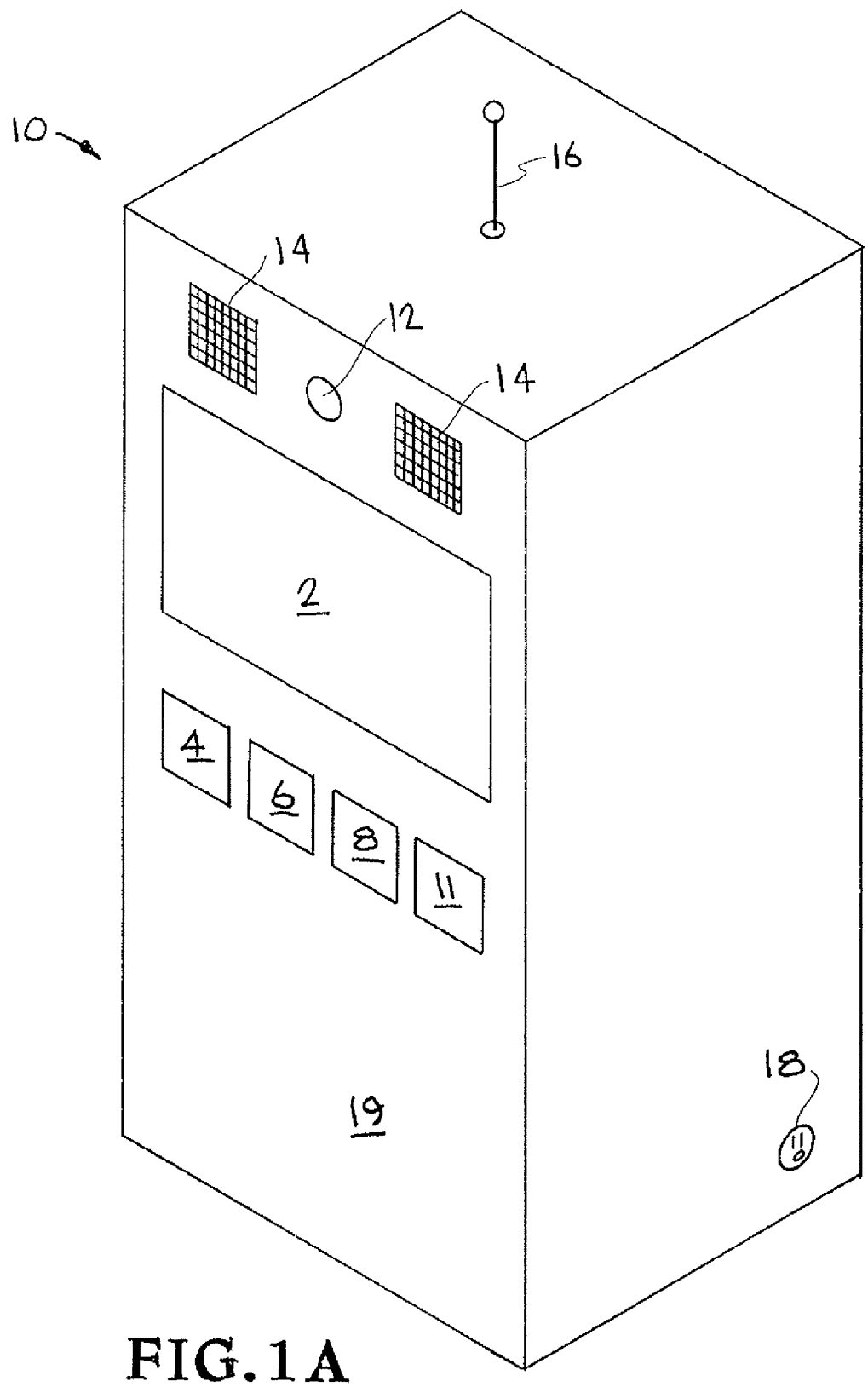
FIG. 1 illustrates one embodiment of an Autonomous Diagnostic Vending Machine (ADVM).

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The present invention provides a diagnostic apparatus for analyzing samples from patients. The diagnostic apparatus includes a body unit; a sample acquisition unit in the body unit that acquires samples from patients; a diagnostic instrument in the body unit that analyzes samples and produces diagnoses for the patients, and a control in the body unit that is connected to the sample acquisition unit and the diagnostic instrument. The diagnostic apparatus can be described by various titles including a "diagnostic kiosk or station for diagnosing diseases." Another title for the diagnostic apparatus is: "Autonomous Diagnostic Vending Machine (ADVM)." Other titles for the diagnostic apparatus are: "Laboratory in a Box (LIAB)," "Autonomous Diagnostic Unit (ADU), "Autonomous Clinical Diagnostic Laboratory Box (ACDLB)."

INTRODUCTION

Autonomous Diagnostic Vending Machines (ADVMs, 10) are fully-equipped, self-service diagnostic instruments. ADVMs contain robotic equipment to dispense collection vials (40) to users interested in having a biological sample analyzed for a disease, syndrome, or condition. A user collects and places a biological sample (e.g. nasal swab) into a collection vial that is submitted into an ADVM for automated diagnostic services. The ADVM performs molecular analysis on a portion of the submitted sample and archives the remaining sample for possible further confirmatory testing. Depending on the degree of use, ADVMs can operate for more than a month without requiring maintenance. ADVMs provide many of the same services available from advanced clinical diagnostic laboratories. They are ideal for all types of settings, ranging from busy emergency rooms where these instruments can help triage patients, to rural settings where sending samples to remote diagnostic laboratories is both time consuming and costly. ADVMs are also equipped with video-telemedicine capabilities that enable doctors to see and speak with individuals in remote areas that do not have immediate access to specialists. In addition, ADVMs may be placed in public locations (e.g. pharmacies) and equipped with pay station capabilities to enable the general public to provide a co-payment fee for access to an ADVM's diagnostic services, without having to make an appointment to see a physician.

ADVMs (10) deployed to publicly accessible areas such as pharmacies, may prove to be an effective way to reduce overcrowding in emergency rooms and also help reduce the overall cost of delivering healthcare. A user of a publicly deployed ADVM can return to the comfort of their home to wait for their results, which may take less than one hour from the time the sample was deposited in the machine. Results can be electronically delivered to the user via email, text message, pager, or through to a secure website. Prior to or just after receiving results, users may also receive a phone call from a remotely-located physician (240) that monitors ADVM data. The monitoring physician, equipped with a positive diagnosis from the ADVM, is better prepared to prescribe the proper medication or suggest an over-the-counter remedy that may help alleviate the user's symptoms than a physician seeing a patient for the first time in person for whom a diagnosis has not yet been determined. The placement of ADVMs in pharmacies makes picking up medications for diagnosed illnesses especially convenient since prescriptions can be wired directly to the hosting pharmacy. Likewise, individuals infected with untreatable non-life-threatening diseases may be advised to rest at home and not return to work until their infection has passed. For instances where the diagnosis is more dire or inconclusive, remotely-located ADVM monitoring physicians can advise these individuals to either wait for an ambulance to arrive, or immediately transport themselves to the nearest hospital that has been notified in advance of their arrival and is prepared to receive them.

ADVMs (10) provide an extremely convenient, fast, and affordable way to receive a diagnosis for some illnesses. The limitations of ADVMs are dependent on several factors, including the whether the diagnostic instrument (20) housed within the ADVM is capable for performing the requested assay, and whether the sample requires professional assistance to be collected. The later limitation is overcome by placing ADVM in medical facilities where professionals can collect samples from sick individuals. Pharmacies hosting ADVMs may choose to hire a healthcare professional (e.g. registered nurse) to assist users in collecting samples so more types of diseases, syndromes, and conditions can be screened. For situations where ADVMs are stationed in areas without medical professionals, the choice of samples collected and assays performed would be limited accordingly. If the suspected illness requires professional assistance to acquire the biological sample, remotely-located physicians can use the ADVM's tele-medicine capability to speak to users and advise them as to where they may go to receive proper medical care for their suspected conditions. For diseases in which sample collection is not an obstacle, the ADVM provides a questionnaire to users regarding their symptoms and the history of their illness, and this information is plugged into an algorithm that determines the assay most likely to yield a positive diagnosis for the causative agent, considering the geographic region, time of year, and recently diagnosed infections. The ADVM's automated decision making process can be overridden by a tele-medicine linked-in physician that requests a specific assay to be performed.

DESCRIPTION OF THE DRAWING FIGURES

Figure 1B:
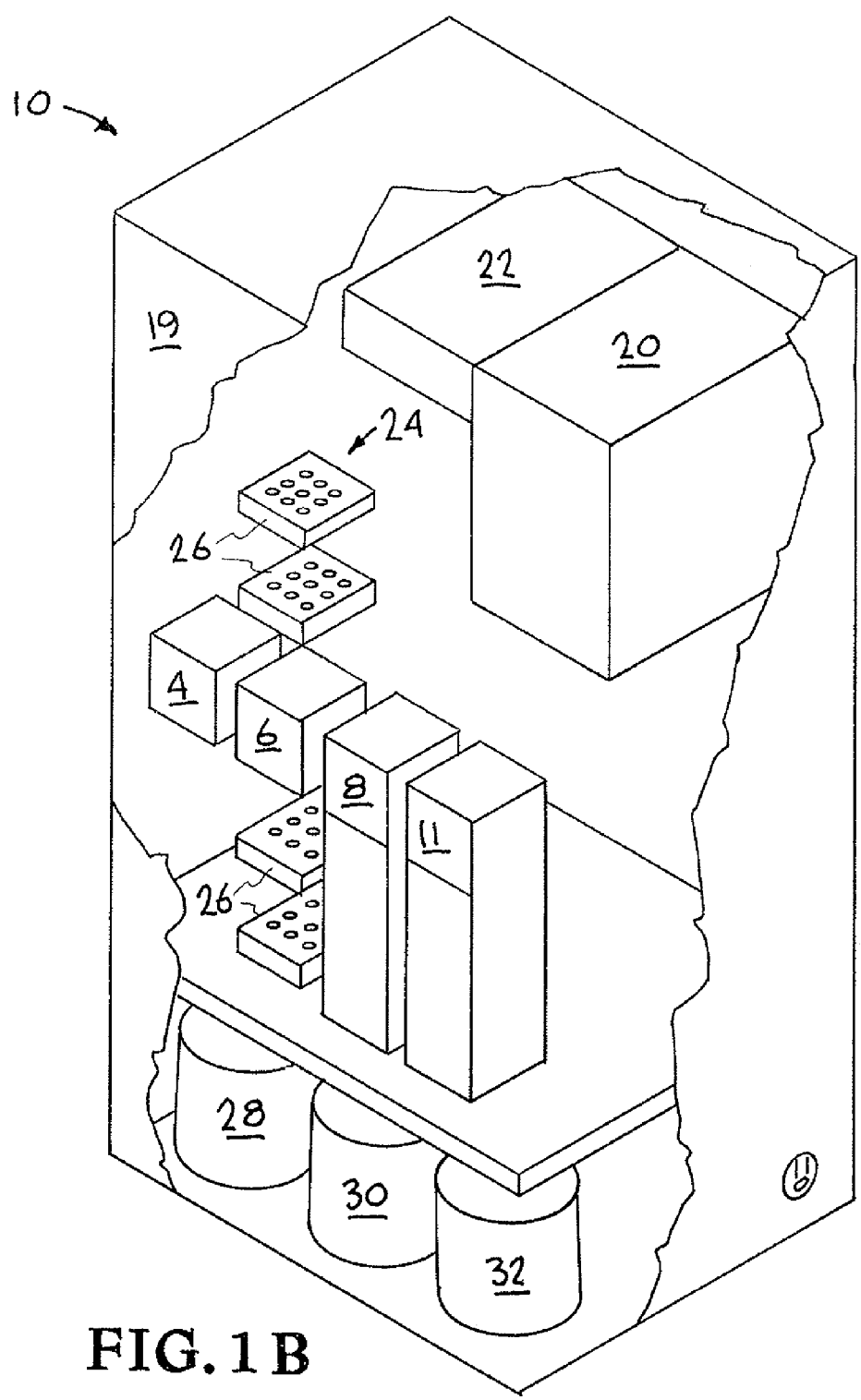

In FIG. 1A and FIG. 1B an example of one embodiment an Autonomous Diagnostic Vending Machine (ADVM, 10) is shown.

An Autonomous Diagnostic Vending Machine (10) is similar in size and shape to a soda vending machine. An AVDM is composed of a computer (22), touch-screen monitor (2), collection kits (38) and vials (40); machinery to dispense collection vials to users, receive the collected sample vials, and delivered them to an automated multi-channel diagnostic instrument (20) for automated processing; a video camera (12) with audio capabilities (14), a pay station (11), and a waste receptacle (8).

The touch-screen monitor (2) serves as a communication link between the user and the ADVM's internal computer (22). A user may also choose to communicate with the ADVM through wireless Bluetooth or infrared 'beaming' of information by handheld devices (e.g. PDA or cell phone). The touch-screen monitor also serves as a telemedicine video screen. A video camera (12) mounted above the touch-screen monitor is associated speakers (14) and an embedded microphone (14) that allows remotely-located physicians to see and speak with users to discuss treatment options. The video screen may also be used to play tutorials, show commercials, and access specific internet web pages.

The anatomy of the ADVM (10) is described as follows: right and left sides, anterior and posterior sides; superior (top) and inferior (bottom) ends. The motor movements are described in the X, Y, and Z dimensions (e.g. 'X'=horizontal–left/right movement, 'Y'=horizontal–anterior/posterior movement, and 'Z'=vertical–inferior/superior movement). For example, the touch-screen monitor (2) is located in the anterior position along the centerline of the instrument, and the pay station (11) is shown on the anterior left side of the instrument (the vantage point from the ADVM, not from the user of the ADVM).

Figure 3:
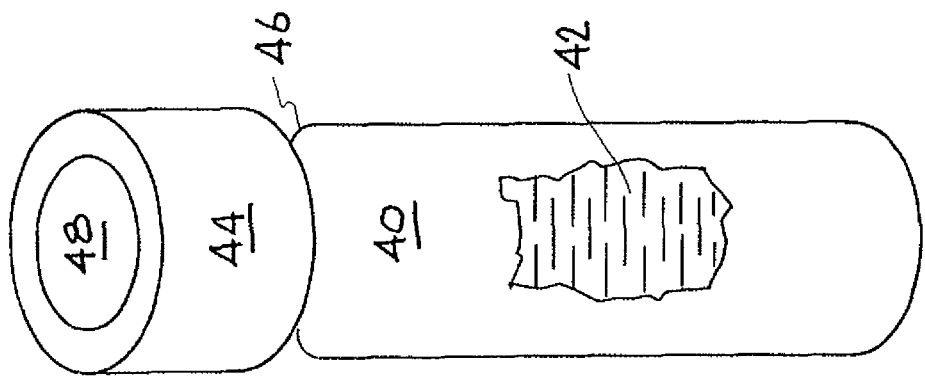
FIGS. 2 and 3 illustrate the collection vial and collection kit of an ADVM.
Figure 2:
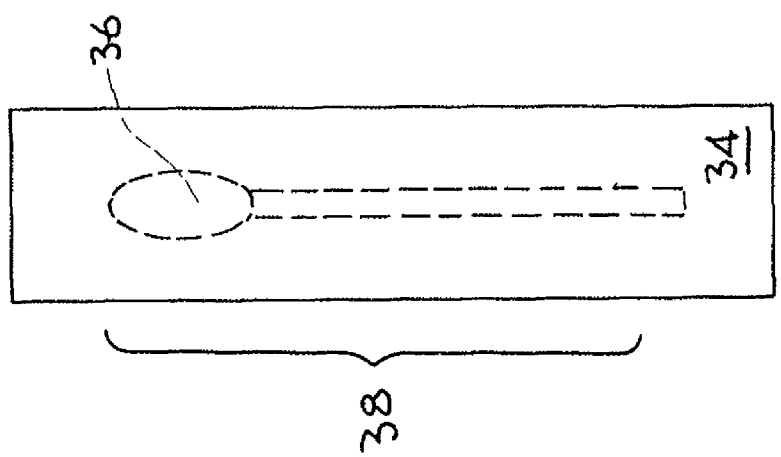

The components of the Autonomous Diagnostic Vending Machine (ADVM, 10) shown in FIGS. 1A and 1B are as follows:
 Touch-Screen Monitor
 Collection Kit Bay
 Sample Bay
 Waste Receptacle
 Autonomous Diagnostic Vending Machine
 Pay Station
 Video Camera
 Speakers and Microphone
 Internet Connectivity (wireless or wired)
 Power Plug Receptacle
 Outside Casing of ADVM
 Automated Diagnostic Instrument
 Computer/Controller of ADVM
 Tray Tower
 Trays
 Water
 Bleach
 Waste FIGS. 2 and 3 show the collection vial and collection kit of an ADVM (10).

The described embodiment is specifically designed to detect respiratory infections. This ADVM (10) dispenses a collection kit (38) to users that includes a sterile Q-tip-like device (36) encased in protective wrapping that may be effectively used to swab the nasal passageway or throat. In addition, ADVMs dispense 2 mL vials (40) that contain sterile buffered media (42). The vial caps (44) have rubber or silicone septa (48) that can be punctured by needles (156) to access internal media. The term 'collection vial' is used to describe a vial containing sterile buffered media that has not been in contact with a sample. The term 'sample vial' is used to describe a collection vial that contains or has contained a sample derived from a human, animal, plant, or an environmental source.

The components of the collection vial and collection kit are as follows:
 Protective Wrapping
 Q-Tip-like Device
 Collection Kit
 Vial
 42—Buffered Media
 43—Cap of Vial
 46—Neck of Vial
 47—Septum of Cap Other embodiments can easily be envisioned that test for multiple different types of diseases, syndromes, or conditions, using a wide range of sample collection kits (38). The collection kits are unlimited in the scope of materials they may contain, including: gloves, sterile swabs (36), alcohol swabs, iodine swabs, band-aids, aspirin, Tylenol, drugs, medications, syringes, nucleic acid extraction cartridges and cleaning cartridges, different types of vials (40) or containers, as well as tools and sample preparation kits to aid in the collection of samples. Samples that may be collected and introduced to the ADVM (10) include, but are not limited to mucus, sputum, skin cells (cheek swab), blood, pus, fecal matter, cerebral spinal fluid, tears, semen, vomit, genital secretions, water, air, environmental samples, and food.

Figure 4A:
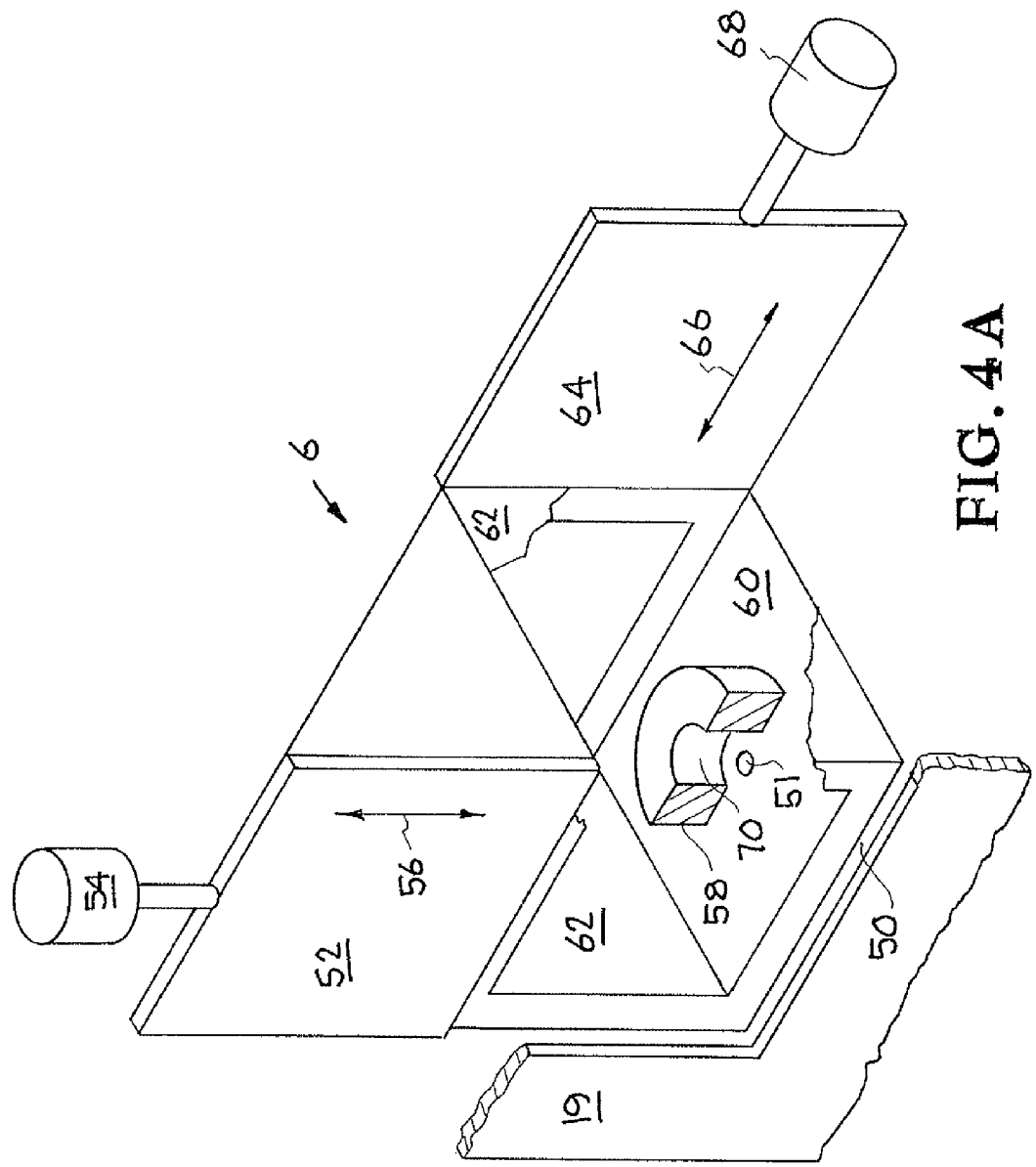
FIGS. 4A and 4B illustrate the sample and collection kit bays of the ADVM.
Figure 4B:
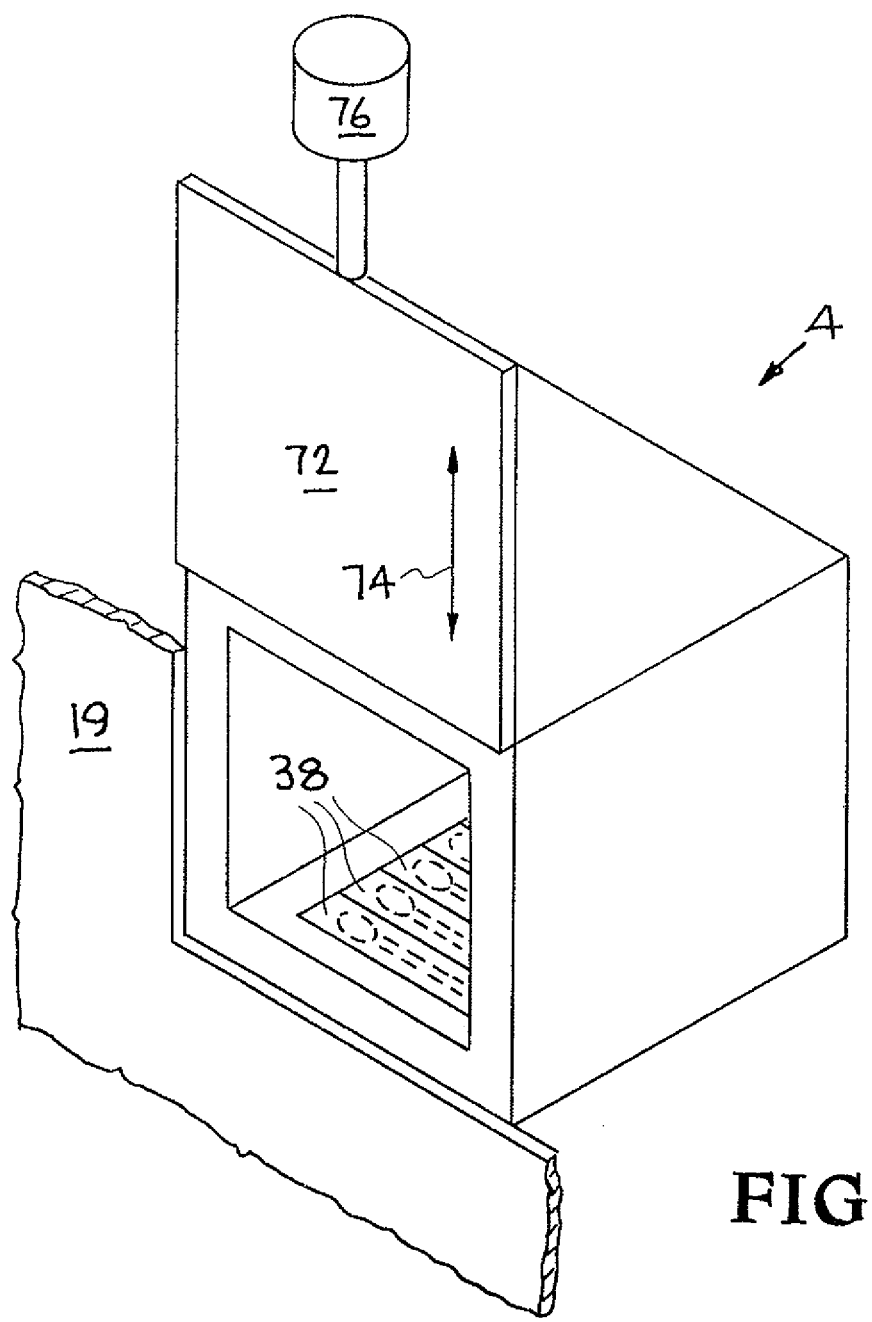

FIGS. 4A and 4B show the sample and collection kit bays of the ADVM (10).

The front of the ADVM (10) contains two separate doors (52 & 72, FIGS. 4A & 4B) that are used to control access to the sample (6) and collection kit bays (4). The sample bay is used as a transfer location where the instrument places collection vials (40) for the users to pickup and later drop off their collected samples for the ADVM to analyze. The collection kit bay is where users pickup collection kits needed to help collect samples in a sterile manner. The two doors limit access to each location to registered users who have submitted a co-payment fee or received a user password. The opening and closing of each door is controlled by linear motors (54 & 76). Access to the bays is controlled to prevent dust and particulate matter from entering the machine and prevent non-paying users from taking sample collection kits (38). The closing of the doors is monitored by optical and pressure sensors that protect users from harm.

The anterior sample bay door (52, FIG. 4A) is connected to the outside casing (19) of the ADVM (10). Behind the anterior door, is the sample bay (6), which is a moveable component inside the ADVM. The sample bay is comprised of a floor (60), two sides (62), a roof, a vial holder (58), and a motor-controlled posterior door (64). The posterior door of the sample bay is always closed when the anterior door is open. The closed posterior door prevents users from reaching into the inner recesses of the ADVM when the anterior door is open. The sample bay contains a vial holder in the middle, which is used by the instrument to drop off and pick up vials.

The collection kit bay (4, FIG. 4B) is used to dispense collection kits (38) to users. These kits are freely available to users once the door (72) has opened, but may also be individually dispensed in an automated fashion.

Figure 5:
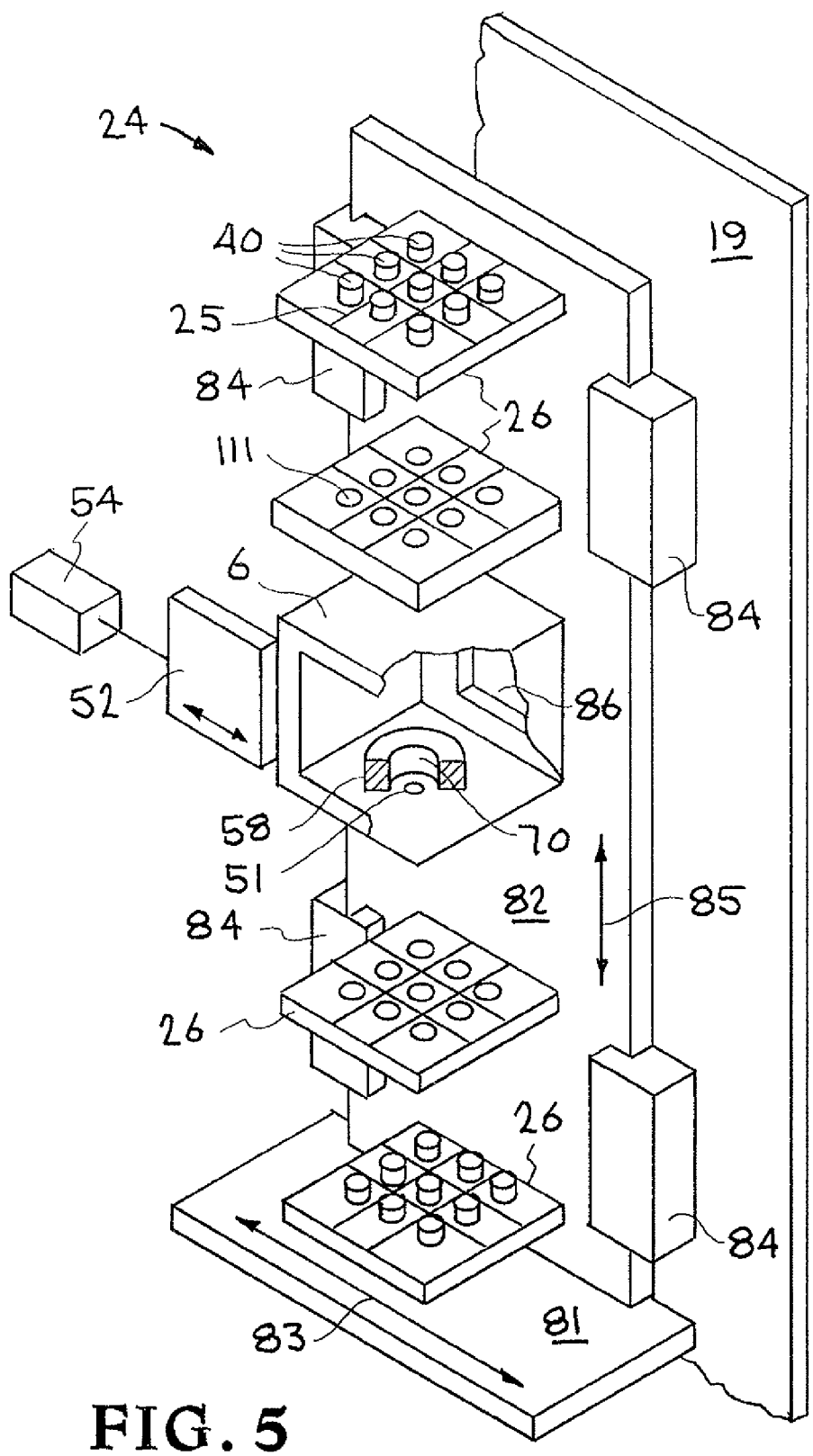
FIG. 5 illustrates the tray tower of the ADVM.

The components of the sample bay and collection kit bay are as follows:
- 4—Collection Kit Bay
- 6—Sample Bay
- 19—Outside Casing of ADVM
- 38—Collection Kits
- 50—Gap between Outside Casing and Sample Bay
- 51—Underside Hole of Vial Holder
- 52—Anterior Sample Bay Door
- 54—Motor Controlling Anterior Sample Bay Door
- 56—Direction of Movement of Anterior Sample Bay Door
- 58—Vial Holder
- 60—Floor of Sample Bay
- 62—Wall of Sample Bay
- 64—Posterior Sample Bay Door
- 66—Direction of Movement of Posterior Sample Bay Door
- 68—Motor Controlling Posterior Sample Bay Door
- 70—Top Hole in Vial Holder
- 72—Collection Kit Bay Door
- 74—Direction of Movement of Collection Kit Bay Door
- 76—Motor Controlling Collection Kit Bay Door FIG. 5 shows the tray tower of the ADVM (10).

The tray tower (24) is an internal component of the ADVM (10), which is not directly accessible to users. The tray tower includes the sample bay (6), but is largely composed of multiple trays (26) that hold collection and sample vials (40). These trays are mounted to a Z platform (82) connected to a slide (84) that moves in the vertical direction through the action of a linear stepper motor (85). The number and size of the trays is only limited by the size of the trays and the size of the ADVM. Likewise, the number of vials (40) each tray holds is dependent on the size of the vials and the dimensions of the tray. For easy of illustration, the example shows 9 vials per tray. The vials are held in place by partitions (25) within the trays. Underneath each vial is a hole (111) in the tray that is of a smaller diameter than the diameter of the vial.

Trays (26) are positioned along the Z platform (82) above and below the sample bay (6). The sample bay is mounted to the same Z platform, but there is a hole (86) in the platform that allows access into the sample bay from the anterior direction (i.e. from the front of the ADVM). Since the trays and sample bay are connected, they move in the same direction. Of note, the outside casing (19) of the ADVM (10) has a sample bay door (52) that opens and closes but is stationary in comparison to the entire sample bay connected to the tray tower, which moves up and down and from side to side. The outside sample bay door only opens when the anterior opening of the sample bay (86) is lined up with the anterior sample bay doorway on the outside casing (19).

The Z platform (82) to which the tray tower (24) and sample bay (6) are mounted is part of a directional motor assembly that itself is mounted to an X platform (81) near the bottom of the ADVM (10). The X platform is connected to a slide that moves (83) in the left to right direction, along the base of the ADVM, just inside the outside casing.

The components of the tray tower assembly are as follows:
- 6—Sample Bay
- 19—Outside Casing of ADVM
- 25—Partitions
- 26—Tray
- 40—Vial
- 52—Posterior Door of Sample Bay
- 54—Motor Controlling Posterior Door of Sample Bay
- 58—Vial Holder
- 70—Top Hole in Vial Holder
- 78—Tray Tower
- 81—X Platform
- 82—Z Platform
- 83—Direction of Movement of X Platform (X Motor)
- 84—Slide
- 85—Direction of Movement of Z Platform (Z Motor)
- 86—Anterior Opening to Sample Bay
- 111—Hole in Tray FIGS. 6A, 6B, 6C, and 6D show the vial acquisition head of the ADVM (10).

Figure 6A:
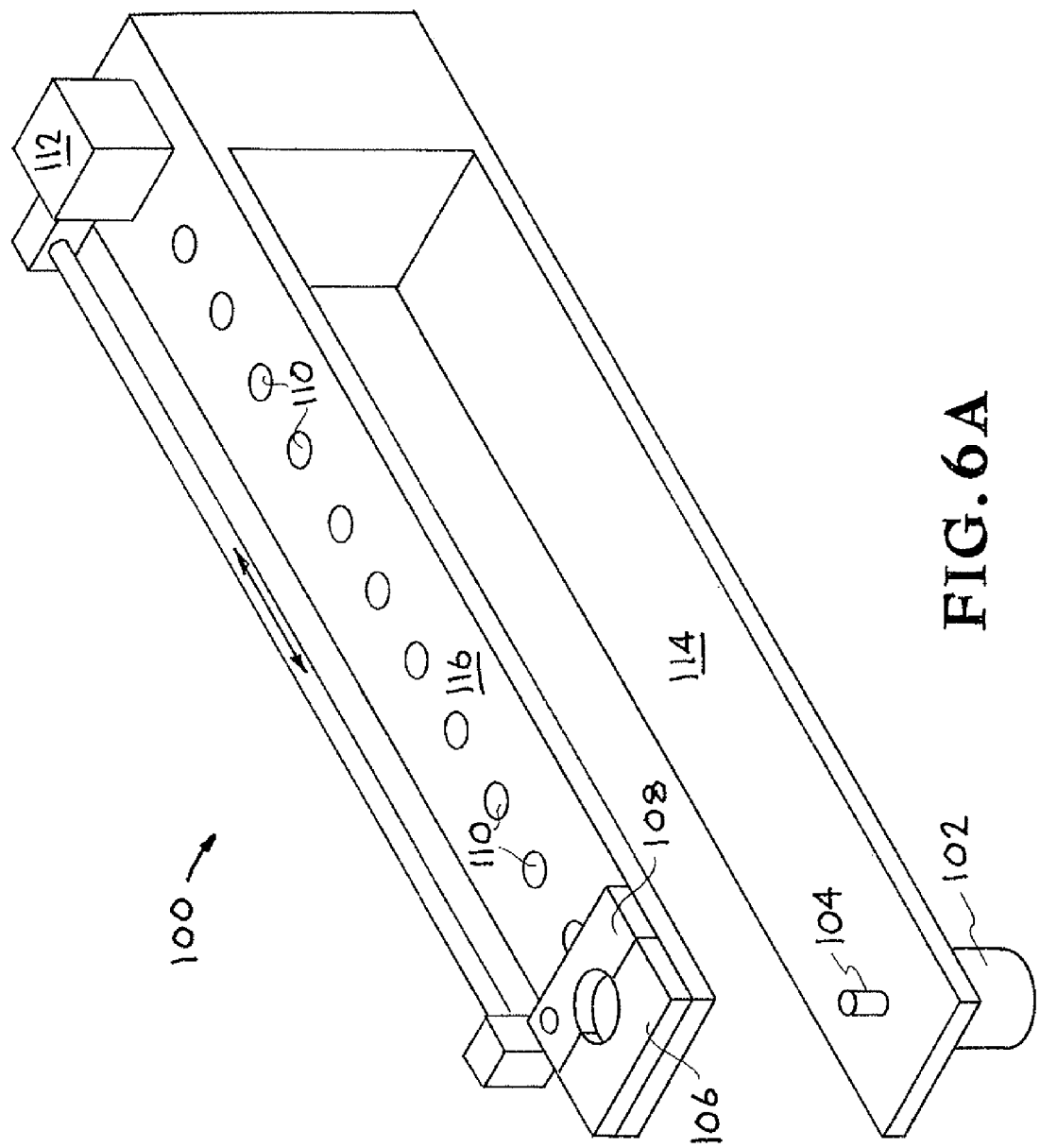
Figure 6B:
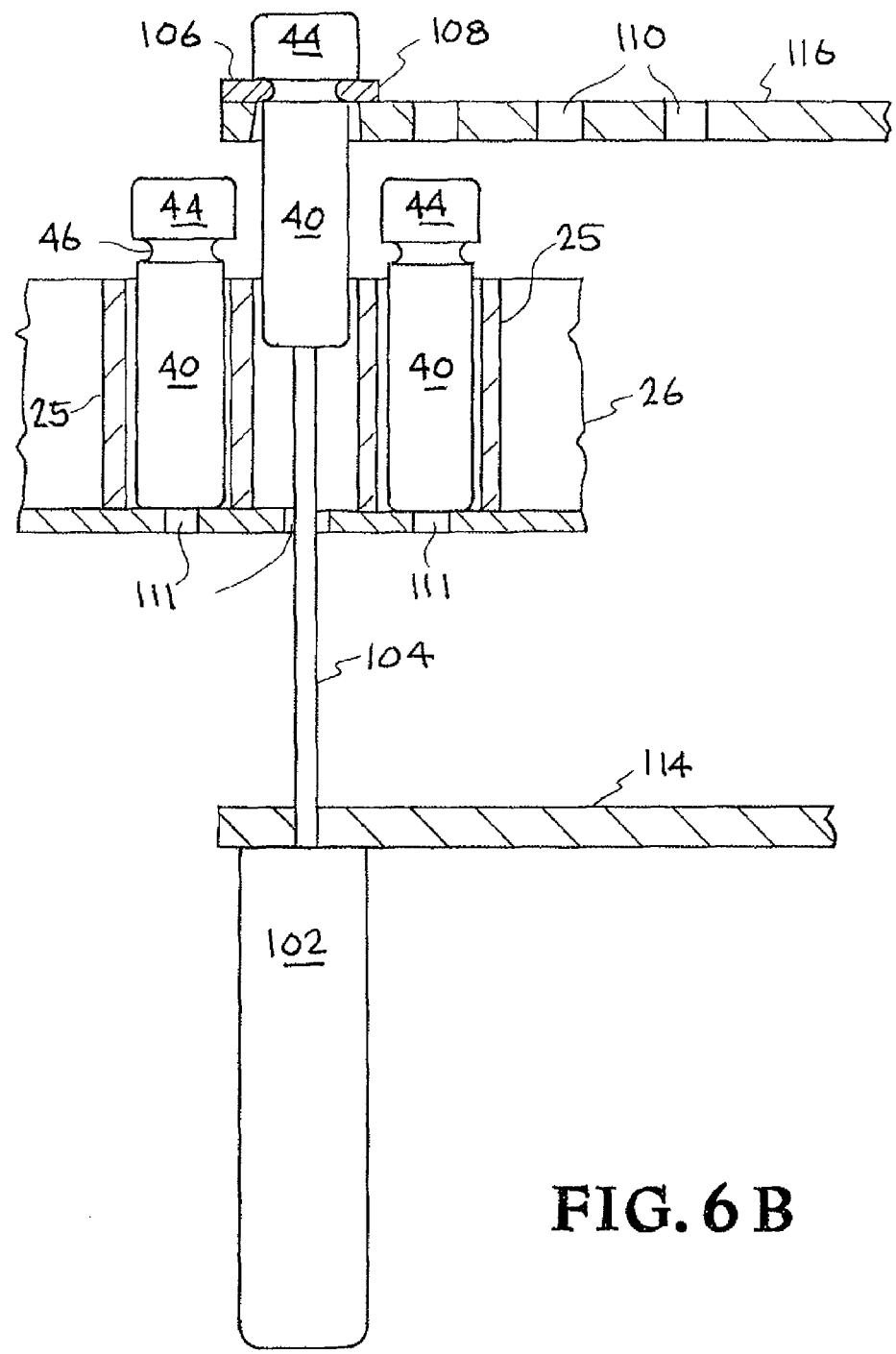
Figure 6C:
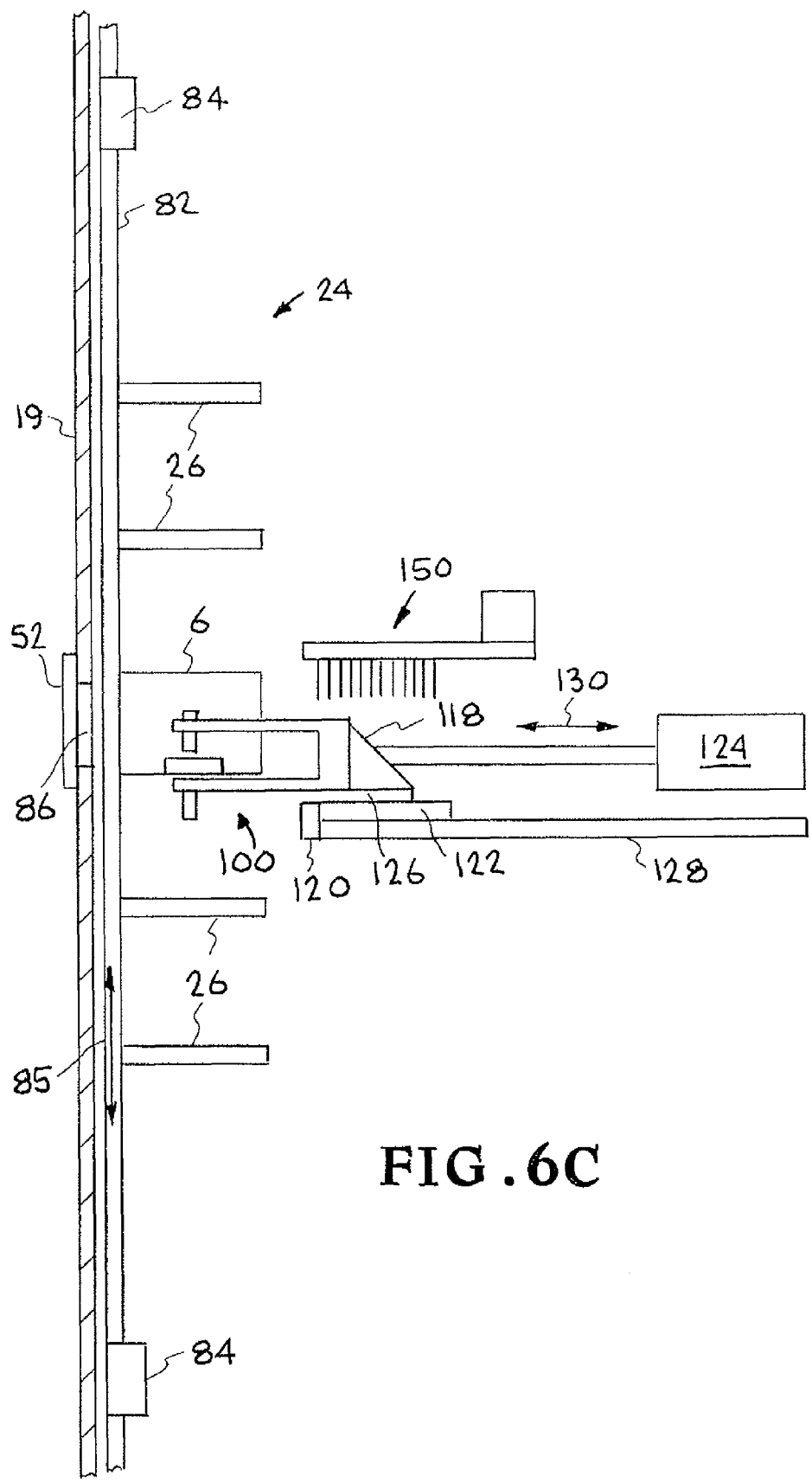

FIG. 6A shows the acquisition head (100). FIG. 6B shows the acquisition head (100) removing a vial (100) from a tray (26). FIG. 6C shows the acquisition head (100) picking up a sample vial (40) deposited by the user in the sample bay (6). FIG. 6D shows the acquisition head (100) retracted and positioned beneath the needle bank (150, FIG. 7), which descended to draw in a portion of the sample, and the tray tower (24) has lowered to a position where the acquisition head can extend and deposit (archive) the vial into a tray (26).

The vial acquisition head (100, FIG. 6A) is composed of upper (116) and lower (114) jaws that work in concert to pickup and place vials (40) from either the vial holder (58, FIG. 4A) or a vial tray (56, FIG. 6B). The vertical distance between the upper jaw and lower jaw is not quite double the height of a tray filled with vials, which is equivalent to distance between the underneath side of the sample bay floor (60) and the top of a vial placed in the vial holder (58, FIG. 4A). The jaw's opening is slightly deeper than the depth (anterior to posterior axis) of the trays and sample bay (6, FIGS. 6C & 6D). The width of the acquisition head is smaller than the width of the sample bay (left to right axis). Then entire acquisition head is mounted on a Y platform (126), which is connected to a slide (122) that runs from posterior to anterior within the ADVM (10), stopping just shy of the rear of the tray tower (24) and sample bay (6, FIGS. 6C & 6D). The terminal mount (120) of the Y-axis linear motor assembly (130) near the tray tower is supported by a structural beam (128) that connects the left and right sides of the ADVM. The acquisition head mounted on the Y platform is constructed to extend in the anterior direction, beyond the confines of the mount that limits the Y platform's anterior movement. The over-extended head reaches into the vicinity of the trays and sample bay; positioning the upper and lower jaws above and below a particular vial in a tray or the sample bay's vial holder. The acquisition head is able to access every vial held within the tray tower, by adjusting the positions of the X (81), Y (120), and Z (82) platforms that affect the location of the acquisition head and the tray tower.

The lower jaw (114) of the acquisition head (100) contains a stepper driven screw actuator (102) that vertically extends a piston (104, FIG. 6B). The piston's diameter is small enough to fit through the holes (111, FIG. 6B) in the trays as well as the hole (51) in the sample bay's vial holder (58, FIG. 5). A properly positioned acquisition head is able to extend the piston to elevate a vial (40) out of its holding place (FIG. 6B). The elevated vial rises up through a hole in the upper jaw (116) of the acquisition head so that the neck (46) of the vial is in the same plane as the upper jaw. The vial is kept upright through partial support from the vial partitions (25) in the tray (26) and also the upper jaw. The hole in the upper jaw through which the vial rises is adjustable in size. The hole is made up of two half-moon structures that face each other (FIG. 6A). The distal half-moon plate (106) is a fixed component of the upper jaw, whereas the proximal half-moon plate (108)

moves under the control of a linear motor (112). The positioning of the proximal plate, in relation to the distal plate, determines the size of the hole. The closing of the proximal half-moon plate around the neck of a vial secures it in the upper jaw. Once secured, the piston associated with the lower jaw can be retracted. To completely free the vial from the tray, it is necessary to lower the tray tower slightly, so the bottom of the vial clears the tops of the other vials in the tray (FIG. 6B).

The upper jaw (116) has 12 evenly spaced holes (110) along the length of the jaw (FIG. 6A). The hole at the tip of the jaw is adjustable, whereas the 11 others are fixed in size. Holes are placed in the upper jaw when the internal diagnostic instrument (20, FIG. 8) is able to process more than one sample at a time.

Figure 7:
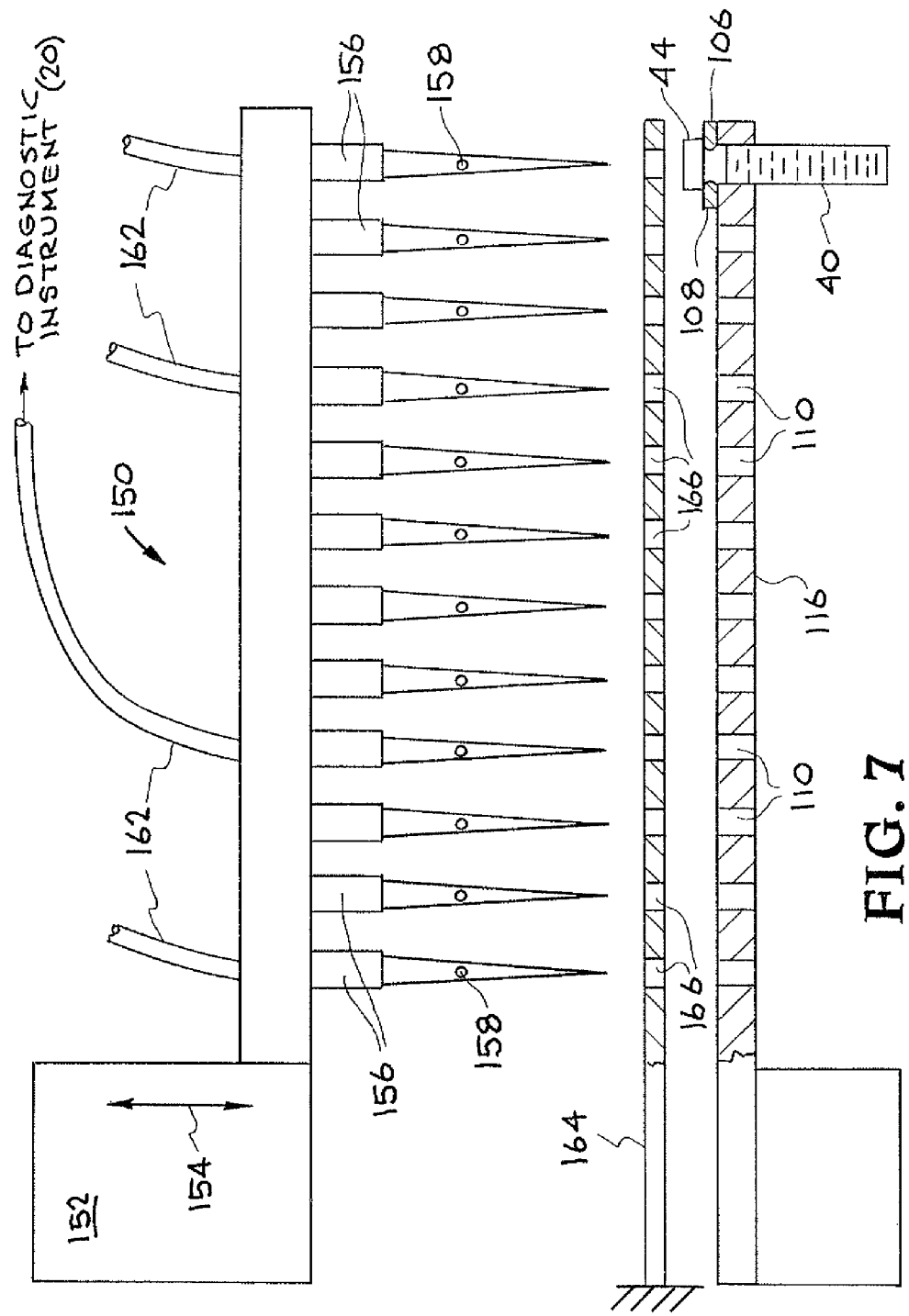
FIG. 7 illustrates the needle bank of the ADVM.

The components of the acquisition head are as follows:
6—Sample Bay
19—Outside Casing of ADVM
25—Vial Partition
26—Tray
40—Vial
44—Cap
46—Neck
82—Z Platform
84—Slide
85—Direction of Movement of Z Platform (Z Motor)
100—Acquisition Head
102—Linear Motor for Piston
104—Piston
106—Distal Fixed Half-Moon Plate
108—Proximal Movable Half-Moon Plate
110—Holes
111—Holes in Tray
112—Linear Motor for Movable Half-Moon Plate
114—Lower Jaw
116—Upper Jaw
118—Support Structure
126—Y Platform
122—Slide
124—Screw Actuator
120—Mount at End of Screw Actuator
128—Support Beam
130—Direction of Movement of Acquisition Head (Y Motor)
150—Needle Bank (FIG. 7)

Many different types of mechanical, magnetic, or pneumatic mechanisms can be envisioned that enable the acquisition head (100) to grasp a vial (40) aside from the mechanism mentioned above. Other examples include a pincher style claw or a circular solenoid grasper that constricts around the neck (46) of the vial. In addition, sensors can be incorporated to ensure proper execution of each desired function. Pressure sensors can be used to ensure sufficient force is applied to secure the vial, but not so much as to damage the vial or clasping mechanism. Optical or weight sensors may also be used to determine whether a vial has been successfully moved.

FIG. 7 show the needle bank of the ADVM (10).

This example describes an AVDM (10) that can process twelve samples at a time. This type of instrument generally requires a syringe pump (200) for each sample that can be processed. Each syringe pump (200, FIG. 8) is connected to a hollow needle (156, FIG. 7) by tubing (162). The sample is collected when the tip of the needle pierces the vial's rubber septum (48, FIG. 3) and suction is applied through the tubing to draw a portion of the sample into the diagnostic instrument for analysis. Although there are twelve needles in this instrument, the sample bay (6, FIG. 4A) of the described AVDM only accepts one sample at a time. A sample placed in the sample bay is picked up by the acquisition head (100, FIG. 6A) and positioned underneath one of the 12 needles of the diagnostic instrument. Rather than having each needle descend independently of one another, which would require twelve separate directional motors, it is easier to mount all the needles to a common structure (160) that is moved under the control of just one motor (152, FIG. 7). The upper jaw of the acquisition head has twelve holes (1 adjustable+11 fixed) to permit passage for each of the twelve needles through the upper jaw, although just one of the twelve needles will actually pierce the cap (44) of the vial (40) secured in the upper jaw's most distal hole.

The needles (156, FIG. 7) of the diagnostic instrument (20, FIG. 8) are sharp and sturdy enough to repeatedly pierce the rubber septa (48) found in the sample vial caps (44), without requiring frequent replacement. Each needle has one or more holes (158, FIG. 7) in the sides or tip that permit the suction of fluid through the needle and into the diagnostic instrument. A protection bar (164) with twelve holes (166) is fixed beneath the needle bank (150). Descending needles pass through this protection bar to access the acquisition head (100), which is positioned in the same orientation as the needle bank. When the needle bank is retracted, the tips are safely behind the bar. The protection bar provides a mechanical safety barrier for technicians servicing ADVMs (10), and furthermore, provides an additional physical barrier to ensure the vial (40) becomes separated from the piercing needle during retraction, should the upper jaw (116) of the acquisition head fail to securely grasp the vial.

Figure 8:
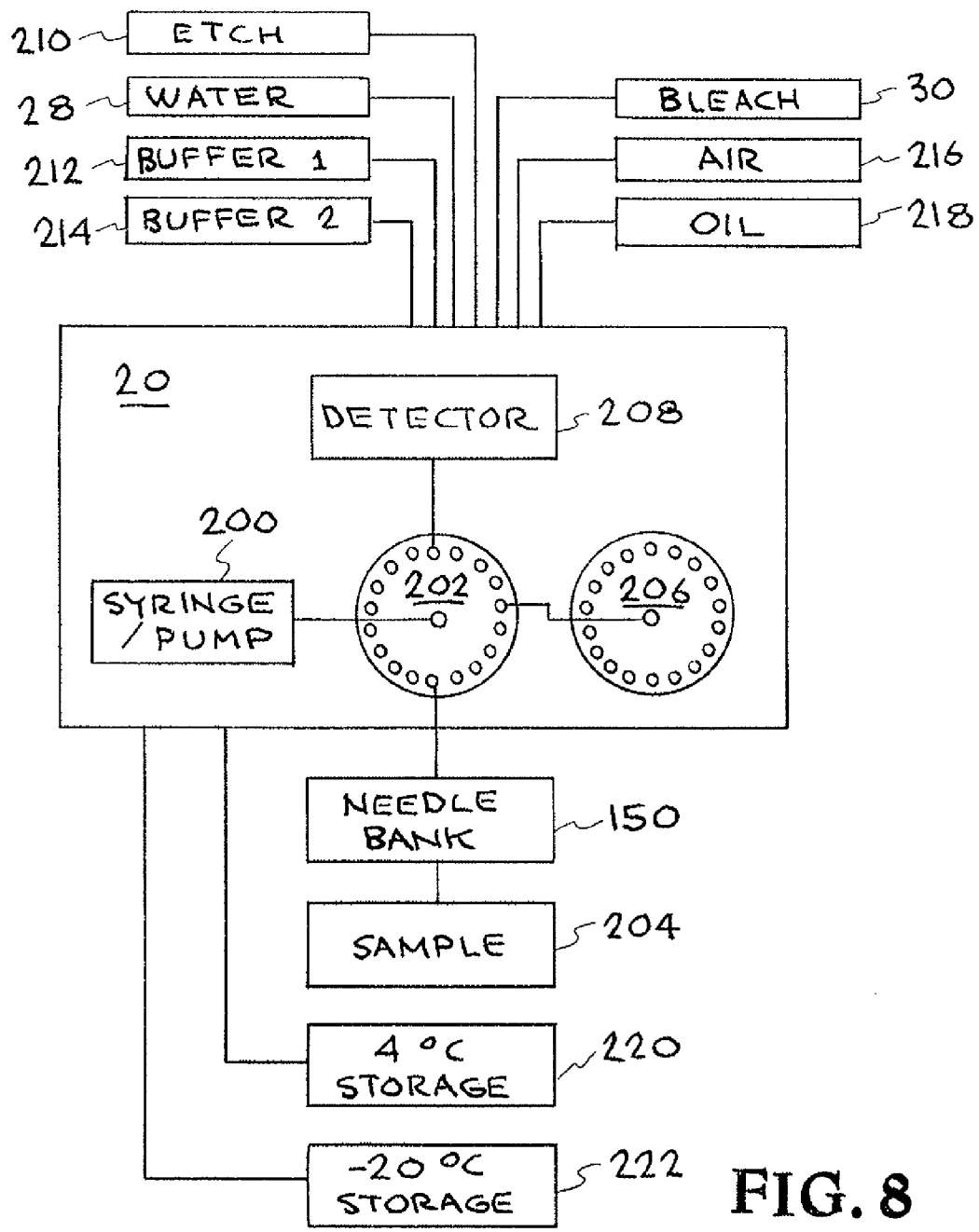
FIG. 8 illustrates the diagnostic instrument of the ADVM.

The components of the needle bank are as follows:
40—Vial
44—Cap
106—Distal Fixed Half-Moon Plate
108—Proximal Movable Half-Moon Plate
110—Holes
116—Upper Jaw
150—Needle Bank
152—Motor
154—Direction of Movement of Needle Bank
156—Needle
158—Holes in Needle
160—Support Structure
162—Tubing (Lines)
164—Protective Bar
166—Holes FIG. 8 shows the automated diagnostic instrument of the ADVM (10).

ADVM (10) can be designed to include any type of automated diagnostic (20) instrument as long as the instrument performs assays that utilize liquid samples stored in vials (40). Many complex matrices can be liquefied including tissues, exudates, sputa, nasal swabs, pus, blood, urine, fecal matter, sweat, etc. Diagnostic instruments that perform antibody-based assays, aptamer-based assays, liquid chromatography, gel electrophoresis, and mass spectrometry, sequencing, and similar diagnostic assays can easily be envisioned.

The automated diagnostic instrument (20) within the ADVM described here is a high throughput flow-through real-time instrument as described and claimed in the U.S. Provisional Patent Application No. 60/904,505 filed Mar. 2, 2007 by John Frederick Regan titled "Automated High-Throughput Flow-Through Real-Time Fluorescence Detector" referenced in the Cross Reference to Related Applications section above and in U.S. patent application Ser. No. 12/038,109 title "Automated High-Throughput Flow- Through Real-Time Diagnostic System" by John Frederick Regan filed Feb. 27, 2008. This instrument is capable of processing 12 samples in an asynchronous, simultaneous, and parallel fashion for an unlimited number of genetic sequences. The instrument is extremely sensitive as it performs nucleic acid extraction and purification before performing the genetic assay. This diagnostic instrument is capable of detecting pathogens (viruses, bacteria, fungi, molds, parasites, etc.) as well as identifying the presence of genetic mutations that may cause cancer, syndromes, and diseases. The diagnostic instrument utilizes multiple different liquid buffers and reagents to complete its assays. Some of these buffers such as water (28), bleach (30), ethanol (210), lysis buffer (212), and elution buffers (214) are stable at room temperature. This particular diagnostic instrument also utilizes reagents that are heat-labile reagents (e.g. primers, probes, and enzymes), which must be stored in either the 4° C. (220) or −20° C. (222) compartments to maintain their activity for longer periods of time. Likewise, archived sample vials (40, FIG. 3) that contain samples should be stored at either 4° C. or −20° C. to preserve the sample, should additional confirmatory or exploratory testing be performed. These different temperature zones are part of the ADVM, and are designed to extend the length of time during which the ADVM can operate without a drop in the quality of the assays performed or the integrity of the stored samples.

Figure 9:
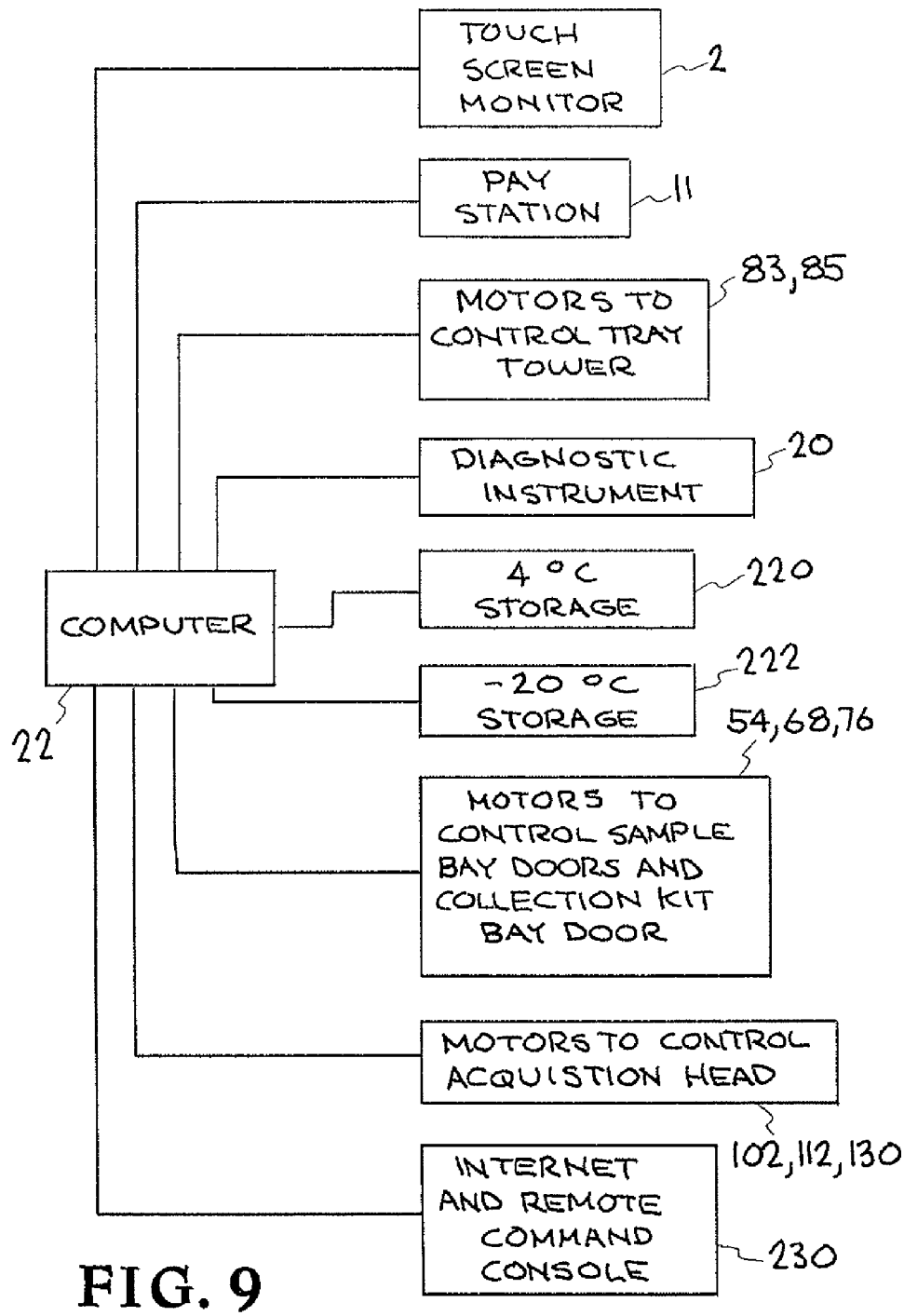
FIG. 9 illustrates the communication network within the ADVM.

Components of the diagnostic instrument are as follows:
    20—Diagnostic Instrument
    28—Water
    30—Bleach
    150—Needle Bank (FIG. 7)
    200—Syringe Pump
    202—Sample Valve
    204—Sample Line
    206—Reagent Valve
    208—Detector
    210—Ethanol
    212—Buffer 1
    214—Buffer 2
    216—Air
    218—Oil
    220—4° C. Storage
    222—−20° C. Storage FIG. 9 shows the communication network within ADVM (10).

The ADVM's computer (22) receives commands directly from users who communicate through the system's touch screen monitor (2, FIG. 1A). For situations in which the a co-payment is required for services, the ADVM's computer verifies the receipt of the co-payment with the pay station (11) before proceeding with dispensing a collection kit (38, FIG. 2) and vial (40, FIG. 3) to the user. The ADVM's computer coordinates dispensing each vial, which includes orchestrating the actions of roughly 7 motors associated with the vial tray tower (24, FIG. 5), acquisition head (100, FIG. 6A), and bay doors (52 & 72, FIGS. 4A & 4B). Likewise, when each sample is received and delivered by the acquisition head (100) to the diagnostic instrument for analysis, the ADVM's computer relays the requested assays to be performed by the diagnostic instrument to the diagnostic instrument's computer.

The components of the communication network within an ADVM include the following:
    2—Touch-Screen Monitor
    11—Pay Station
    20—Diagnostic Instrument
    22—Computer/Controller of ADVM
    54—Motor to Control Anterior Door of Sample Bay
    68—Motor to Control Posterior Door of Sample Bay
    76—Motor to Control Door to Collection Kit Bay
    83—X Motor to Control Tray Tower
    85—Z Motor to Control Tray Tower
    102—Motor to Control Piston on Acquisition Head
    112—Motor to Control Size of Hole in Upper Jaw of Acquisition Head
    130—Motor to Control Y Platform of Acquisition Head
    220—4° C. Storage
    222—−20° C. Storage
    230—Remote Command Console and Internet Hook-up FIG. 10 shows the communication network surrounding the remote command console.

ADVMs (10) may be stationed in local hospitals (252), staffed pharmacies (254), and unstaffed locations (256). Data generated from all field-deployed ADVMs can be automatically uploaded into a remote centralized database that is part of the remote command console (230). Physicians (240) and epidemiologists can compile and review that is being generated in real-time. These data can be used to determine trends in infections regionally, nationally, and worldwide. These instruments can be incorporated into infectious disease surveillance systems already established (e.g. the Department of Defense's Global Emerging Infections System (GEIS) System). These data can be used to quickly identify areas potentially exposed to a bio-terrorist attack or areas in which a natural deadly infection has been detected. Officials can use these data to identify the affected area(s), helping focus containment and treatment efforts, which may include 'ring' vaccinations, prophylactic drug treatment, and medical care. Furthermore, widely deployed ADVMs would provide clues as to when an unknown pathogen has emerged, which would be suspected if a spike in the number of unidentified infections is reported. The remote command console would be able to report to the CDC (250) any startling findings.

Figure 10:
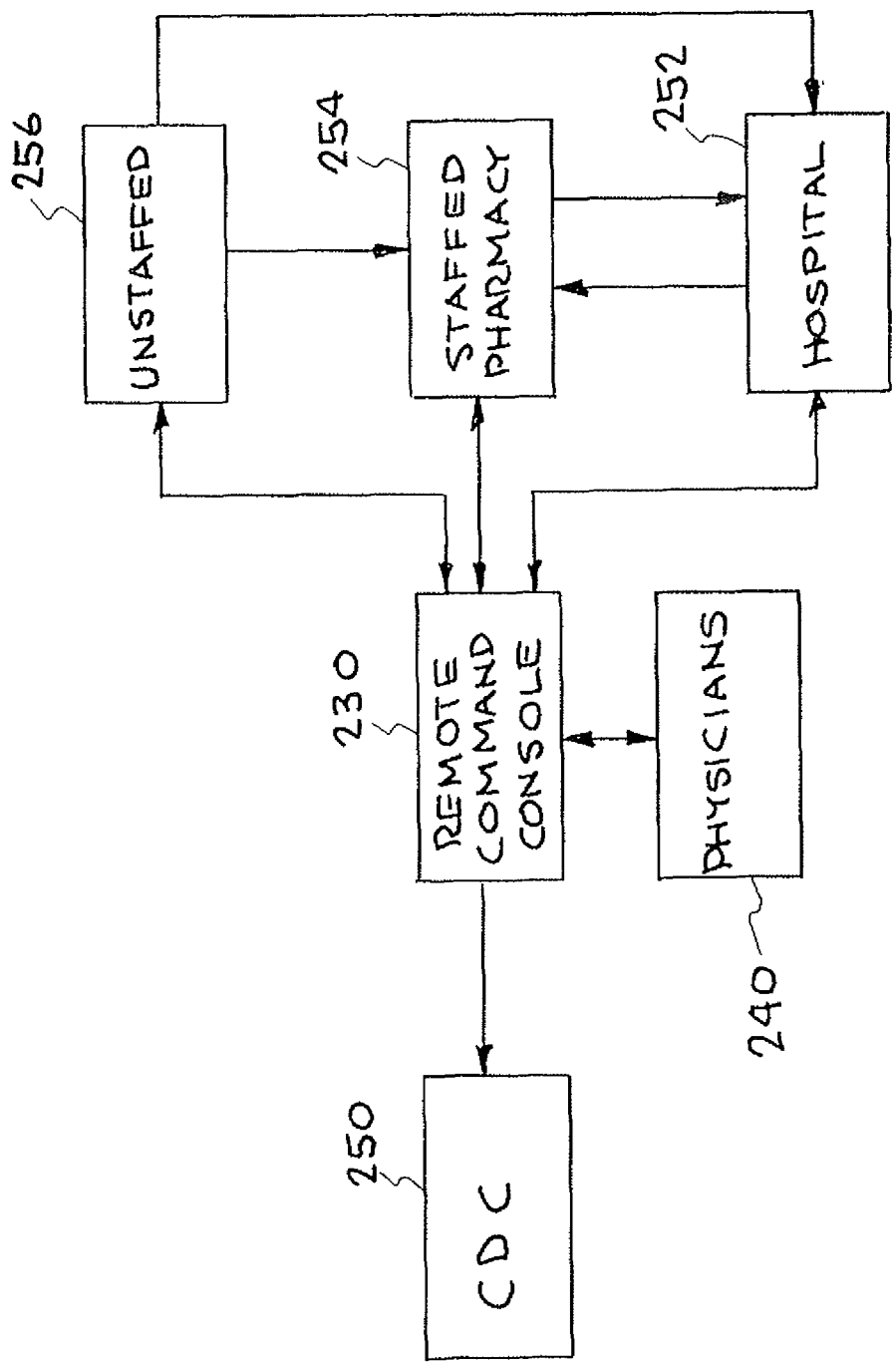
FIG. 10 illustrates the communication network between the remote command console, central database, ADVMs, hospitals, and the CDC.

The components of the communication network shown in FIG. 10 are as follows:
    230—Remote Command Console (RCC)
    240—Physicians Monitoring RCC
    250—Centers for Disease Control and Prevention (CDC)
    252—ADVM at Hospitals and Medical Facilities
    254—ADVM at Staffed Pharmacies
    256—ADVM at Unstaffed Locations Operation Description of ADVMs Sample Collection: An individual suffering from a respiratory infection and interested in receiving a diagnosis, would approach an ADVM (10) and register as a user to receive a collection vial (40, FIG. 3) and sterile Q-tip-like device (36, FIG. 2). Alternatively, an individual that is unable to travel, but is in need of a diagnosis, can ask a family member, friend, or home healthcare provider to go to the nearest ADVM and request a collection vial and kit on their behalf. If the sick individual visits an ADVM in person, he/she may choose to collect their sample directly in front of the machine or return to the privacy of one's own car or home to collect the sample. If the user chooses to collect the sample in privacy, or is running the errand for another, the user would log out of the ADVM to allow others to access the instrument in his/her absence. When the user is ready to collect his/her sample (or aid in collecting someone else's sample (e.g. infirm relative at home)), the user removes the sterile Q-tip device from its protective wrapping (34) and swabs the inside of their nasal cavity or the back of their throat to obtain a sample. The user would then unscrew the cap (44) of the collection vial and stir the sample-laden Q-tip in the sterile media (42) to transfer the pathogens present on the Q-tip into the liquid media. The user then removes the Q-tip device and screws the cap back onto the base of the vial. The collection vial is now called a sample vial. The sick individual (or errand runner) can return the sample vial to an ADVM for processing. To avoid re-registering, those returning the sample vial must log in with the same username and password used to originally acquire the collection vial (38) and kit.

ADVMs (10) are designed to be operated by either the lay public or trained professionals (e.g. hospital workers). The descriptions of the mechanistic operation of the instrument is the same for both, however, the computer user interface would be altered slightly to suit the educational level and experience of the anticipated user/operator. The following description of operating an ADVM is provided from the vantage point of being a naïve user accessing an ADVM in a locale where professional assistance is not available.

ADVM Registration

A naïve user approaches the invention and is greeted with a welcoming screen on the touch-screen monitor (2, FIG. 1A) that gives the user several touch-button choices, including: preferred language, tutorial describing the ADVM's capabilities, and an area to register as a new client or proceed as a returning client. The user would be prompted through several screens that would cover registration including selecting a username and password, medical history, insurance, co-payment, symptoms, type of sample to be collected, recently traveled destinations, desired pathogens to be screened, liability waiver/indemnification page, etc. Return users logging in to an ADVM to retrieve their data would simply enter their username and password to skip directly to their results. Once users have entered all the necessary data, the ADVM's computer sends several commands to internal motorized components to provide the user with a collection vial (40, FIG. 3) and kit (38, FIG. 2). Registration may also be done over the internet to reduce time spent in front of the ADVM. Data from registered users is saved, so that returning users do not need to enter the same information twice, but simply update any outdated information and provide new information as to their current illness. Users that want advice from one of the many remotely-located physicians (240, FIG. 10) that monitor field-deployed ADVMs, may choose to connect to a physician at any time during or after registration. This is achieved by pressing a button on the touch-screen monitor (2, FIG. 1A) that is appropriately labeled "speak to a remotely-located physician". Touching this button activates the ADVM's telemedicine capabilities, which includes turning on the video camera (12), microphone (14), and speakers (14). A remotely-located physician receives this signal and links-into the user's ADVM (10) to discuss face-to-face through the monitor their concerns or questions.

Automated Dispensing of Collection Vial and Kit

The ADVM (10) picks up and drops off vials through the coordinated movement of the tray tower (24, FIG. 5), controlled by X (83) and Z (85) motors, and the acquisition head (100, FIG. 6A), controlled by a Y motor (130). First, the computer (22, FIG. 1B & FIG. 9) sends commands to tray tower's X and Z directional motors to position the tower so the acquisition head can access one particular column of vials (40) within one of the trays (26) held in the tower. The Y platform (120) holding the acquisition head is extended so the upper (116) and lower (114) jaws are above and below the specified tray. The Y platform stops moving when the upper and lower jaws have reached the row location that positions the piston (104) of the lower jaw directly beneath the target vial (FIG. 6A). The piston is extended, raising the designated vial partially out of its holding slot (FIG. 6B). This movement raises the cap (44) of the vial up through the hole in the upper jaw of the acquisition head. The linear motor (112) attached to the upper jaw is extended, thereby clasping the neck (46) of the collection vial. The piston beneath the tray is lowered, and the entire tray tower is lowered slightly so the bottom of the clasped collection vial is above the caps of the other vials held in the tray. The acquisition head holding the claimed vial is now free retract out of the vicinity of the tray tower. The tray tower is then positioned so the sample bay (6, FIG. 6C) is just below being level with anterior sample bay door (52) on the outside of the ADVM's casing (19). This lowered position enables to the acquisition head to extend through the posterior door (64) of the sample bay and have the clasped vial clear the top of the walls of the vial holder (58). Once the clasped vial is positioned over the vial holder, the sample bay is moved up to level with the anterior door, bringing the top hole (70) of the vial holder around the base of the clasped collection vial. The piston is extended through the underside hole (51) of the vial holder, to provide support to the clasped collection vial. The linear motor attached to the upper jaw retracts opening the hole in the upper jaw. The entire acquisition head nudges forward to free the vial completely from the upper jaw of the acquisition head. The piston lowers and the collection vial settles into the vial holder. The acquisition head retracts into the recesses of the instrument and the posterior door of the sample bay closes. The anterior sample bay door opens, and the user is now free to remove the collection vial.

Access to the collection kits (38) is controlled by a separate bay door (72, FIG. 4B). After a user has registered, the collection kit bay door is opened by a linear motor (76) and the user is free to remove a sterile Q-tip-like device (36).

Once the user has removed the vial (40, FIG. 3) and collection kit (38, FIG. 2), the computer (22, FIG. 9) prompts the user to confirm these items have been collected and it is 'ok' to close the sample (52, FIG. 4A) and collection kit bay (72, FIG. 4B) doors. The computer prompts the user to carry out these specific activities both verbally and in writing on the touch-screen monitor (2, FIG. 1A). The computer then prompts the user as to whether they are ready to collect and submit their sample now, or whether they would prefer to log out and return later to have their sample processed.

Submitting a Sample Vial into the ADVM

When a user returns to the invention (10) with a collected sample, he/she encounters the welcoming computer screen (2, FIG. 1A). The returning user logs into the system with the username and password provided during registration. Upon successfully logging in, the sample bay door (52, FIG. 4A) rises and the user is requested to place the sample vial (40, FIG. 3) into the holder (58). The sample bay door closes and a screen notifies the user that their sample is being processed according to the requested assay, and estimates the time of completion.

Introducing the Sample into the Diagnostic Instrument

The mechanism by which the sample vial (40, FIG. 3) is picked up is similar to the mechanism by which the acquisition head (100, FIG. 6A) placed the vial into the holder (58, FIG. 4A), but in reverse. The posterior sample bay door (64, FIG. 4A) opens and the acquisition head extends through the rear of the sample bay (6), and the upper (116, FIG. 6A) and lower (114) jaws are positioned above and below the vial holder (58). The piston (104) is extended to elevate the sample vial into the upper jaw's open hole. The linear motor (112) of the upper jaw is extended to close the half-moon plates (106 & 108) around the neck (46) of the vial. The piston on the lower jaw is lowered, and the sample bay lowers slightly, and the acquisition head is now free retract into the recesses of the instrument (10) without having the bottom of the sample vial clip the top of the vial holder.

The ADVM (10) communicates with the internal diagnostic instrument (20, FIG. 9) to determine which of the twelve channels of the instrument is available for use. This information is relayed to the ADVM's computer (22), which in turn commands the acquisition head (100, FIG. 6A) to stop at one of twelve different locations underneath the needle bank (150, FIG. 7) of the diagnostic instrument, representing an open channel. The bank of needles descends through the protective bar (164) and to a depth that positions the tip of one of the twelve needles (156) near the bottom of the sample vial (40, FIG. 3). The remaining 11 needles are at the same depth, but do not contact anything. The syringe pump (200, FIG. 8) associated with the needle that pierced the sample vial is commanded to draw a portion of the sample into the diagnostic instrument for molecular analysis. Once the diagnostic instrument has acquired enough liquid to perform the requested assay, the bank of needles retracts to its 'home' position.

It is also possible to command the ADVM (10) to introduce portions of the same sample into different channels of the diagnostic instrument (20, FIG. 8) to allow more assays to be simultaneously performed. This approach is particularly useful in situations where the importance of determining the causative agent in the least amount of time possible outweighs the extra cost associated with performing multiple assays at once. In these circumstances, after the needle bank (150, FIG. 7) has retracted and the instrument has begun processing the first portion of sample; the acquisition head (100, FIG. 6A) would position the same vial (40) under another channel of the instrument and the needles (156) would descend again to acquire another portion of the sample to be screened using a different assay. This process could be repeated as many times as the volume of sample permits and the number of channels allows. The automated diagnostic instrument begins processing the sample immediately.

Archiving Sample

The ADVM (10) archives every submitted sample into a tray (26, FIG. 6D). Archiving sample vials (40, FIG. 3) is advantageous for situations in which it may be necessary to perform additional testing within the ADVM on the same sample (e.g. different pathogen panel is screened), or where a professional clinical diagnostic laboratory is interested in performing additional tests on a particular sample that can not be performed by the automated diagnostic instrument (20, FIG. 1B) within the ADVM. In either case, the acquisition head (100, FIG. 6A) must place the sample vial with the remaining fluid into the tray tower (24, FIG. 6C). The vial can either be returned to its original location or placed into a new tray. Placing the used vials into a tray without any sterile collection vials enables service technicians to quickly swap out trays containing used sample vials with fresh collection vials. In this example, the vial will be returned to a fresh empty tray. The process is the same as mentioned for placing a collection vial into the vial holder (58) within the sample bay (6), except the destination is an empty tray.

If the first assay performed on the sample returns a 'negative' diagnosis, the archived sample can be retrieved and another assay can be performed within the ADVM (10) to look for a pathogen that was not screened for during the initial assay. The initiation of secondary screening can be authorized and started by remotely-located physicians, presuming insurance will cover additional tests, or by users willing the pay the extra processing fee. Communications between users and ADVMS can occur directly (i.e. in person) or through a secure internet connection (16, FIG. 1A & FIG. 9).

The ADVM (10) records the identification and location of every sample vial (40, FIG. 3) that is archived. The computer is able to locate a specific vial in the archive (i.e. any designated tray (26)) and deliver it the sample bay (6, FIG. 4A), where a professional may pickup the sample to perform additional testing. This may be particularly important for cases concerning bio-threat agents or lethal diseases. It is also possible to retrieve the files from the ADVM's computer (22, FIG. 9) that describes all the samples in all the trays. The ADVM's computerized system may also be used to organize the tested samples in trays according to a specific diagnosis (e.g. all bacterial infections are stored in tray 'A', all influenza infections are stored in tray 'B', all 'negative' samples are stored in tray 'C', etc.). The ADVM could also be used organizing trays of vials received from an outside source. For example, trays containing randomly positioned but positively diagnosed vials are placed inside the tray tower and the associated computer file describing the contents of each trays is loaded into the ADVM's computer. The ADVM can then be commanded to robotically arranges these samples in any desired manner (e.g. according to diagnosis, age of patient, sex of patient, titer of pathogen, co-infections, separate known from unknown infections, etc.).

Decontaminating the Acquisition Needle and the Sample Line

Once the diagnostic instrument (20, FIG. 8) is free to move fluid through the acquisition needle (156, FIG. 7) without fear of compromising the successful completion of the diagnostic assay, it is necessary to decontaminate the needle used to penetrate the vial (40, FIG. 3) and acquire the sample. To facilitate the decontamination procedure, the tray tower (24, FIG. 5) contains a reuseable decontamination vial that is accessible to the acquisition head (100, FIG. 6A). The decontamination vial has similar dimensions as a collection vial, but is essentially an open-air vessel since there is no septum (48, FIG. 3) through which a needle normally passes. The acquisition head picks up a decontamination vial in the same manner as it would a collection vial and places it beneath the needle to be cleaned. The diagnostic instrument is then commanded to decontaminate the line by sending cleaning solutions through the needle and into the collection vial. The vial can be filled, allowing the outside of the needle to soak in the cleansing reagents. This action decontaminates the needle and prevents one sample from causing a carry-over contamination of the following sample that will be processed using the same sample line (204, FIG. 8) of the instrument. Cleansing agents may include, but are not limited to bleach (30), acetonitrile, detergents, buffers (212 & 214), surfactants, enzymes, and water (28, FIG. 1B & FIG. 8).

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A computer implemented method of diagnosing diseases at hospitals, staffed pharmacies or unstaffed locations for analyzing a vial containing a specimen sample from a user, comprising the steps of:

providing an automated diagnostic vending machine, providing a computer in said automated diagnostic vending machine, providing a diagnostic unit in said automated diagnostic vending machine operably connected to said computer, providing an automated genetic assay diagnostic instrument in said diagnostic unit in said automated diagnostic vending machine that performs nucleic acid extraction from the specimen and produces a genetic assay from the specimen and produces a disease diagnoses, providing a unit for communicating said disease diagnoses to the users in said automated diagnostic vending machine operably connected to said computer and to said diagnostic vending unit, positioning said diagnostic vending machine at the hospitals, the staffed pharmacies or the unstaffed locations, delivering the vial to said automated diagnostic vending machine, using said automated diagnostic vending machine for sample acquisition and processing to perform said nucleic acid extraction from the specimen and produce said genetic assay from the specimen and to produce said disease diagnoses, using said automated diagnostic vending machine for diagnosing diseases from the specimen sample providing said disease diagnosis, using said unit for communicating said disease diagnoses to the users in said automated diagnostic vending machine for communicating said disease diagnosis to the user, and wherein said automated diagnostic instrument in said automated diagnostic vending machine has sample lines, and including the step of decontaminating said sample lines of said automated diagnostic instrument in said automated diagnostic vending machine using cleansing solutions.

\* \* \* \* \*